United States Patent [19]

Grandjean

[11] Patent Number: 5,069,680
[45] Date of Patent: Dec. 3, 1991

[54] MUSCLE STIMULATOR WITH VARIABLE DUTY CYCLE

[75] Inventor: Pierre-Andre Grandjean, Bassenge, Belgium

[73] Assignee: Medtronic, Inc., Minneapolis, Minn.

[21] Appl. No.: 446,794

[22] Filed: Dec. 6, 1989

[51] Int. Cl.⁵ .............................................. A61M 1/10
[52] U.S. Cl. ......................................... 623/3; 600/16
[58] Field of Search .................. 623/3; 600/16, 17, 18

[56] References Cited

U.S. PATENT DOCUMENTS

| | | | |
|---|---|---|---|
| 4,140,132 | 2/1979 | Dahl | 128/419 PG |
| 4,143,661 | 3/1979 | LaForge et al. | 128/419 R |
| 4,384,829 | 5/1983 | Conley et al. | 623/3 |
| 4,453,537 | 6/1984 | Spitzer | 600/17 |
| 4,457,673 | 7/1984 | Conley et al. | 623/3 |
| 4,666,443 | 5/1987 | Portner | 500/16 |
| 4,685,446 | 8/1987 | Choy | 600/18 |
| 4,771,765 | 9/1988 | Choy et al. | 600/18 |

OTHER PUBLICATIONS

Neilson et al., "Left Ventricular Assistance in Dogs Using a Skeletal Muscle Powered Device for Diastolic Augmentation", *Heat Transplantation*, vol. IV, No. 3, May 1985, pp. 343–347.

*Primary Examiner*—Randy Citrin Shay
*Attorney, Agent, or Firm*—John L. Rooney

[57] ABSTRACT

Apparatus and method of controlling a muscle stimulator by varying the duty cycle. The muscle stimulator is particularly adapted to a skeletal muscle powered cardiac assist system. An activity or other sensor is used to determine the requirement for cardiac output. A second electrical sensor is used to determine the cardiac rate. The outputs of these two sensors are employed to select a duty cycle for muscle stimulation of the skeletal muscle. The duty cycle is lowered for reasons of efficiency and safety during periods of very high or very low cardiac rate or body activity. The number of stimulation pulses within a burst is similarly increased when cardiac demand is high to ensure maximum contractile force of the skeletal muscle during each stimulation burst.

9 Claims, 6 Drawing Sheets

MUSCLE STIMULATOR WITH VARIABLE DUTY CYCLE

CROSS REFERENCES TO CO-PENDING APPLICATIONS

This application is related to Ser. No. 07/446,599, filed Dec. 6, 1989, pending, entitled "Steroid Eluting Intramuscular Lead" by the same assignee; Ser. No. 07/446,811, filed Dec. 6, 1989, pending, entitled "Muscle Contraction Control by Intramuscular Pressure Monitoring" by the same assignee; Ser. No. 07/446,592, filed Dec. 6, 1989, pending, entitled "Muscle Work Output Monitor by Intramuscular Temperature Variation Measurement" by the same assignee; and Ser. No. 07/446,593, filed Dec. 6, 1989, pending, entitled "Muscle Fitness Detection by Colorimetry" by the same assignee.

BACKGROUND OF THE INVENTION

1. Field of the Invention

The present invention relates generally to the field of muscle stimulation, and more particularly, relates to monitoring of cardiac assist systems which are powered by skeletal muscle.

2. Description of the Prior Art

Cardiac assist systems do not replace the human heart but merely supplement it. Many techniques have been proposed using a variety of mechanical power sources. Typically these require some form of percutaneous energy transfer, because of the difficulty in storing sufficient energy subcutaneously. Such systems are cumbersome and inconvenient for the patient and are prone to infection along the percutaneous energy transfer path.

A technique holding a great deal of promise is to power the cardiac assist system from a surgically modified skeletal muscle. The cardiac assist system is thus powered by normal biochemical processes. U.S. Pat. No. 4,813,952 issued to Khalafalla teaches a number of configurations of a skeletal muscle powered cardiac assist system. U.S. Pat. No. 4,411,268 issued to Cox teaches a technique for conditioning skeletal muscle to be used in such a cardiac assist system.

Whereas the feasibility of a skeletal muscle powered cardiac assist system has been established in the literature and the clinic, a practical system must address concerns regarding efficiency and safety of operation. Of specific concern is the tying of the rate of stimulation of the skeletal muscle directly to the heart rate. This seems appropriate in some instances, but care must be exercised because of the wide range of possible rates. For example, it may be quite inefficient to stimulate the skeletal muscle at the cardiac rate when the patient is at rest and requires only modest cardiac output. Similarly, it may be inefficient and even dangerous to stimulate skeletal muscle contraction at very high rates. The nature of the skeletal muscle stimulation may also be changed to improve efficiency over the range of available rates and cardiac demands.

SUMMARY OF THE INVENTION

The present invention employs two sensors to control the rate and nature of stimulation of a chronically implanted skeletal muscle powered cardiac assist system. One of the sensors is that which measures the electrical activity of the heart. This sensor would normally be present in any cardiac assist system for purposes of synchronization. It is also used in a demand pacing system to determine natural heart activity. In the present invention this sensor is used to measure cardiac rate. The duty cycle of the skeletal muscle stimulation varies with this measured rate. At very high rates the duty cycle is lowered to improve hemodynamic efficiency and add safety to the system.

The second sensor is used to determine cardiac demand. In the preferred embodiment this is accomplished using an activity sensor although other types of sensors may be used, such as blood oxygen level. During periods of low demand, such as when the patient is at rest and the patient's heart requires little assistance, the duty cycle is lowered to improve overall efficiency. As cardiac demand increases, the duty cycle is increased ensuring that the patient's heart obtains greater assistance at higher loads. Above a very high rate, the duty cycle is again decreased to improve overall hemodynamic efficiency and as a safety measure.

The nature of the skeletal muscle stimulation is also changed with cardiac demand. At low demand levels, the number of pulses in a given burst and the amplitude are decreased to improve efficiency. As demand is increased, pulse count and amplitude are increased to increase the amount of cardiac assistance. Pulse count and amplitude are again decreased at arbitrarily high cardiac rates as a safety measure.

BRIEF DESCRIPTION OF THE DRAWINGS

Other objects of the present invention and many of the attendant advantages of the present invention will be readily appreciated as the same become better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

The present invention employs a sensor to monitor cardiac electrical activity and cardiac demand in a skeletal muscle powered cardiac assist system. The invention uses the output of these sensors to vary a number of parameters of the skeletal muscle stimulation to improve efficiency and safety. The parameters to be varied are duty cycle, pulse amplitude, pulse width, pulse interval, and the number of pulses per burst. The basic cardiac assist system may be configured in a variety of ways as described in U.S. Pat. No. 4,813,952 issued to Khalafalla, herein incorporated by reference. Several of these configurations are discussed herein by way of illustration and are not intended to limit the present invention.

Figure 1:
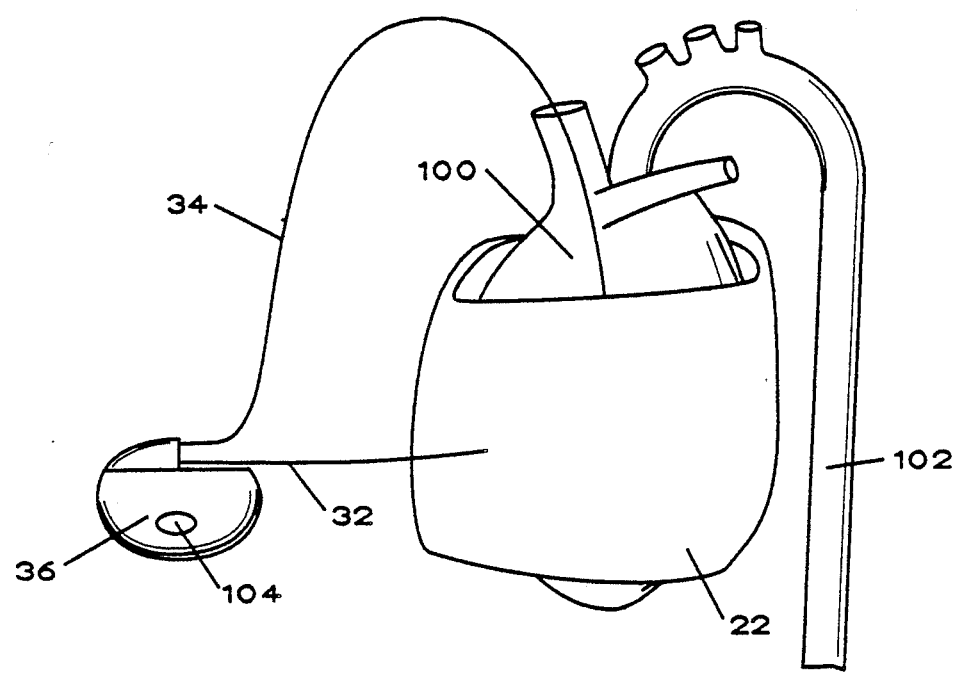
FIG. 1 is a first embodiment of the present invention wherein the skeletal muscle is wrapped about the myocardium.

FIG. 1 is an embodiment of the present invention wherein skeletal muscle 22 is wrapped about human heart 100. Skeletal muscle 22 is conditioned as a "slow twitch" muscle as described by Cox in U.S. Pat. No. 4,411,268, herein incorporated by reference. Implantable pulse generator 36 is coupled to pacing lead 34 to produce a demand pacemaker as taught by Cox. In addition, implantable pulse generator 36 stimulates skeletal muscle 22 to contract in synchrony with human heart 100. Assistance to human heart 100 is provided by the simultaneous contraction of skeletal muscle 22 to increase systolic pressure in descending aorta 102 and elsewhere in the circulatory system.

According to the present invention, implantable pulse generator 36 employs activity sensor 104 in addition to the cardiac activity sensed via pacing lead 34. These inputs are used by implantable pulse generator 36 to adjust the various parameters of the skeletal muscle stimulation regimen as explained below. The parameters to be adjusted are duty cycle, pulse count, and pulse amplitude.

Figure 2:
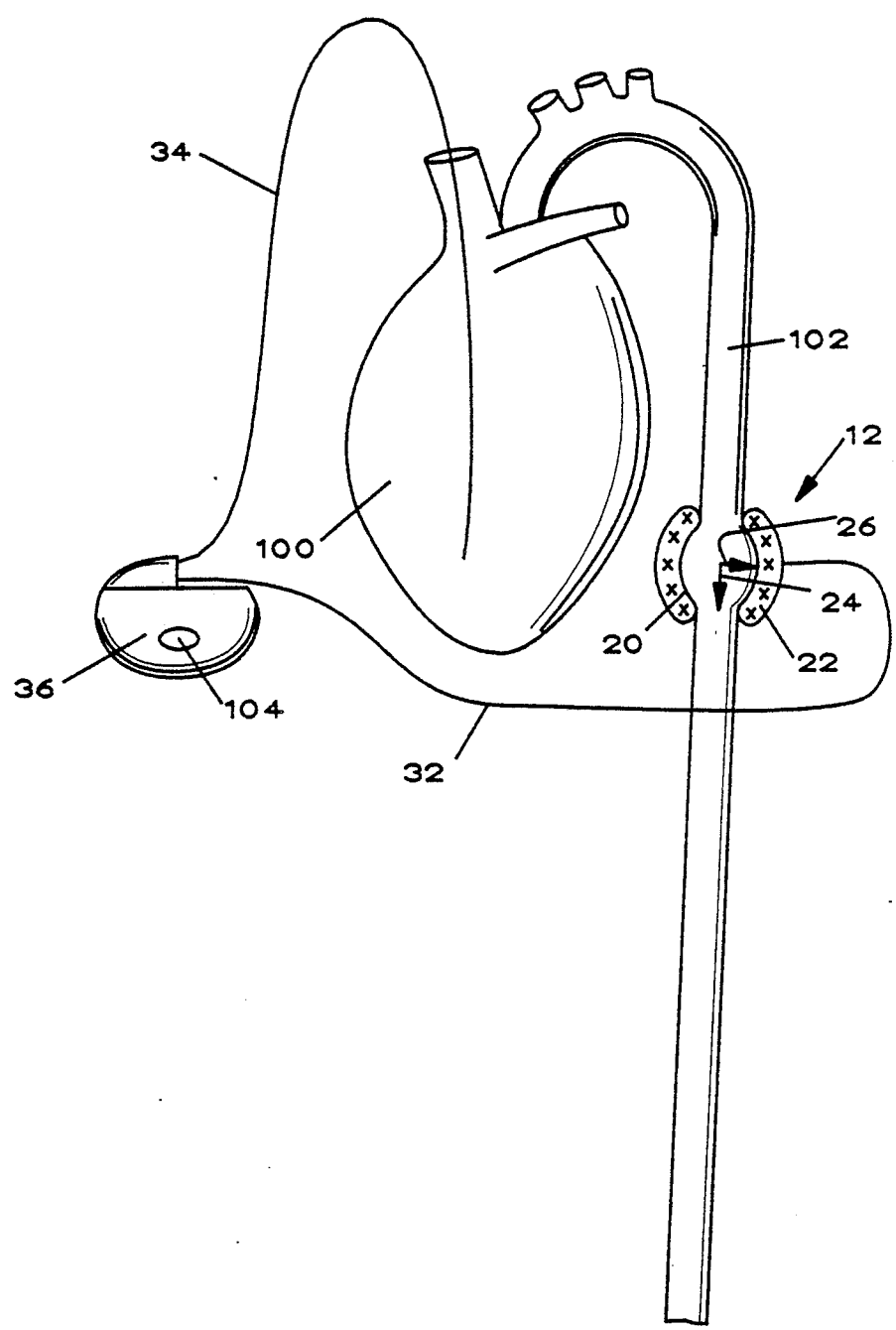
FIG. 2 is an alternative embodiment of the present invention wherein the skeletal muscle is wrapped about the descending aorta.

FIG. 2 is an alternative embodiment of the present invention. In this embodiment skeletal muscle 22 is wrapped about artificial chamber 20 which is inserted in series with descending aorta 102. Unlike the embodiment of FIG. 1, implantable pulse generator 36 stimulates skeletal muscle 22 to contract following evacuation of human heart 100. This is accomplished by the insertion of a delay between a paced or sensed beat of human heart 100 and the stimulation of skeletal muscle 22 as discussed below.

Figure 3:
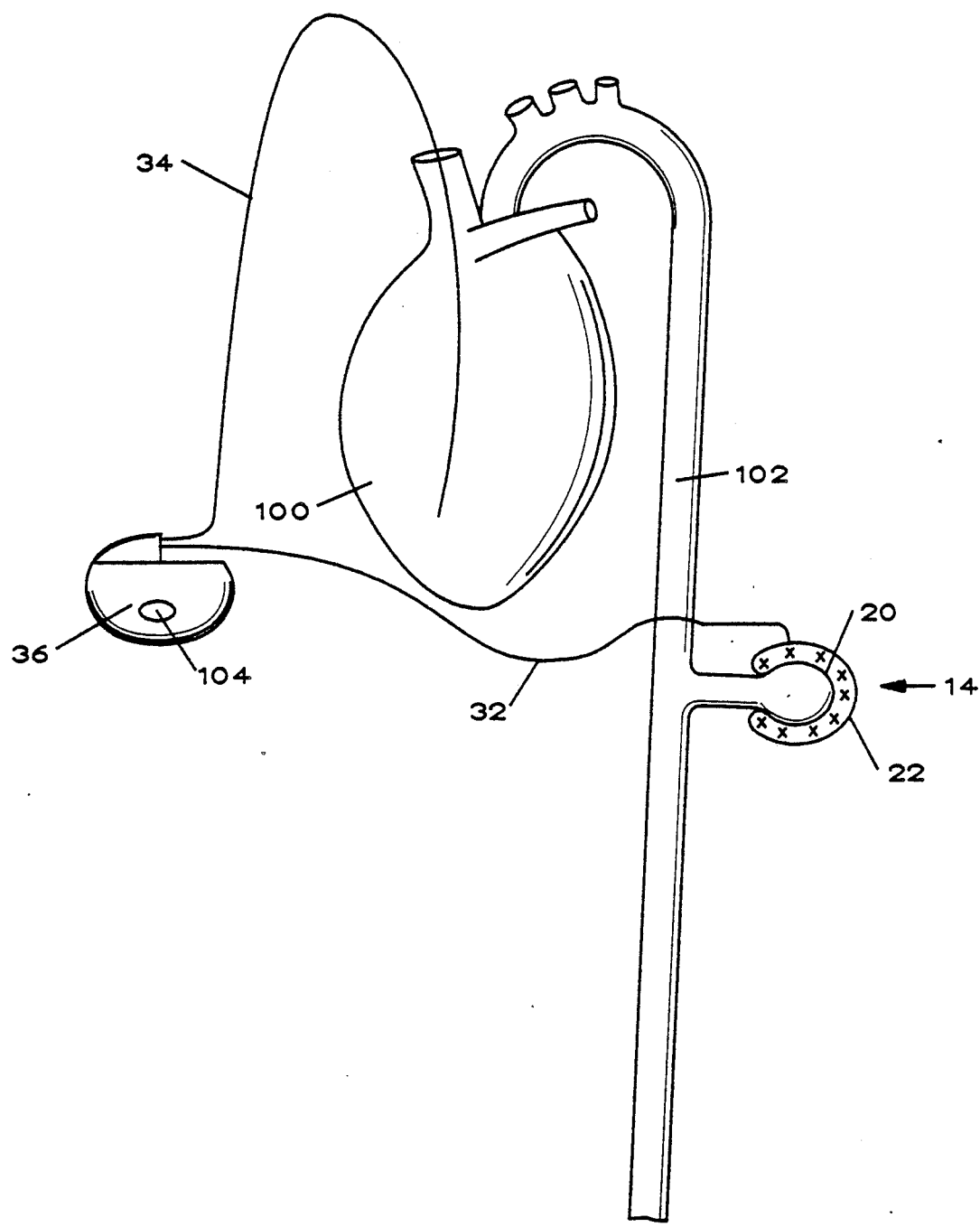
FIG. 3 is an alternative embodiment of the present invention wherein the skeletal muscle performs counter pulsation of the descending aorta.

FIG. 3 is a further embodiment wherein artificial chamber 20 is coupled external to descending aorta 102. In this configuration skeletal muscle 22 is stimulated to counter pulse human heart 100. This raises diastolic pressure, thereby increasing perfusion of human heart 100. This is accomplished by the generation by implantable pulse generator 36 of a sufficient delay, between a sensed or paced contraction of human heart 100 and stimulation of skeletal muscle 22 to cause the desired counter pulsation.

Figure 4:
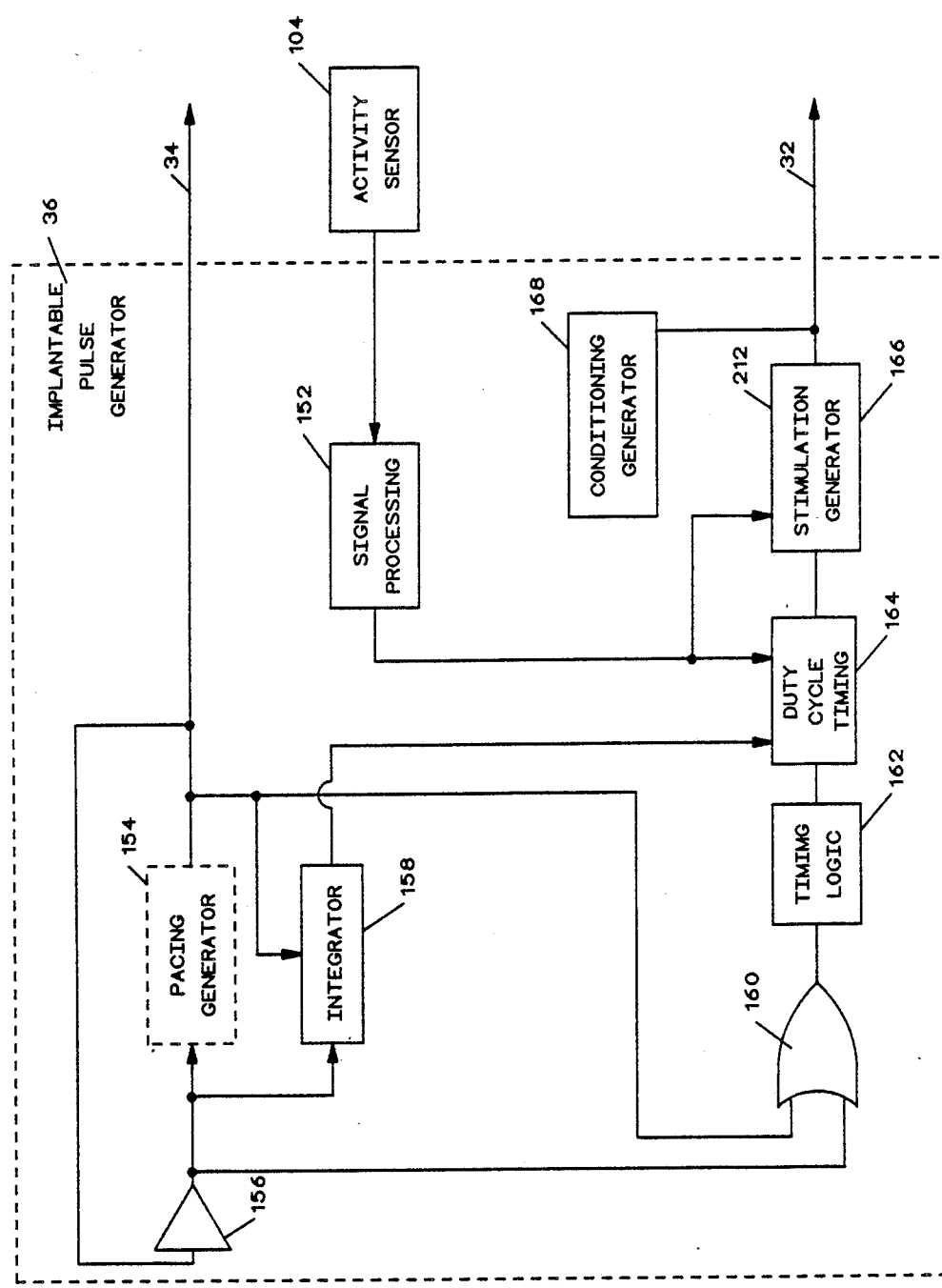
FIG. 4 is a block diagram of the implantable pulse generator of the present invention.

FIG. 4 is a block diagram of implantable pulse generator 36. It includes a pacing generator 154 which operates in the demand mode as is known in the art. Basically, the electrical activity of the patient's heart is monitored via pacing lead 34. Whenever a naturally occurring contraction of the heart is found, sense amplifier 156 detects it and notifies pacing generator 154. If this naturally occurring contraction is sensed within the allotted time, the output of pacing generator 154 is inhibited. However, if pacing generator 154 determines that sufficient time has elapsed since the last contraction of the heart, it produces a pulse which is conveyed to the heart via pacing lead 34 to artificially stimulate the desired contraction.

The main purpose of stimulation generator 166 is to produce a burst of pulses to cause contraction of skeletal muscle 22 in the proper timing relation to the contraction of the patient's heart. To do so, or-gate 160 produces an output whenever sense amplifier 156 senses a naturally occurring contraction or pacing generator 154 supplies an artificial pacing pulse. In either situation, timing logic 162 is started to generate the desired amount of delay. This delay is nearly zero for the embodiment of FIG. 1, because maximum assistance to t e myocardium is provided when skeletal muscle 22 contracts at the same time as the heart.

The embodiment of FIG. 2 requires a much longer delay. This period is on the order of one-half of the cardiac cycle (i.e. R-to-R interval). The embodiment of FIG. 3 requires yet a slightly longer delay, being somewhat greater than one-half of the cardiac cycle. This is necessary because this embodiment is intended to increase diastolic pressure in the aorta.

The output of timing logic 162 is a pulse which is synchronous with the naturally sensed or artificially stimulated contraction of the patient's heart but delayed in time according to the specific embodiment as described above. This pulse is supplied to duty cycle timing circuit 164. This circuit is simply a variable digital counter which produces an output corresponding to a variable number of pulses received from timing logic 162. The normal output of duty cycle timing circuit 164 is one pulse for each pulse received from timing logic 162. This corresponds to the one-for-one stimulation mode of skeletal muscle 22. A lesser ratio of output pulses to input pulses is determined by overall cardiac rate and anticipated cardiac demand.

Overall cardiac rate is determined by integrator 158. It is a circuit which receives inputs from both sense amplifier 156 and pacing generator 154 much as with or-gate 160. In this way integrator is notified of both naturally occurring and artificially paced contractions of the patient's heart. Integrator 158 simply integrates these two signals to produce an average current heart rate. This signal is sent to duty cycle timer circuit 164 to adjust the variable rate counter in a manner which is described in more detail below.

The anticipated cardiac demand may be determined in a number of ways known in the art of cardiac pacing. These include without limitation, measurement of venous blood oxygen level, measurement of blood ph, determination of respiratory rate, computation of minute volume, and measurement of stroke volume. The preferred mode of the present invention uses an activity sensor such as found in MEDTRONIC ACTIVITRAX® pacemakers. Those of skill in the art will readily be able to substitute yet other sensors to determine anticipated cardiac demand.

In the preferred embodiment, an activity sensor 104 is mounted permanently to the housing of implantable pulse generator 36. This activity sensor is preferably a piezo electric crystal which converts mechanical energy received at the housing of implantable pulse generator 36 to electrical energy. It has been sown in the literature that activity sensing in this way is a very good means for anticipating cardiac demand. The output of activity sensor 104 is amplified and integrated by signal processing circuit 152. The result is a signal indicative of anticipated cardiac demand which is transferred to duty cycle timing circuit 164.

The output of duty cycle timing circuit 164 is a pulse train which is a variable number of counts of the output of timing logic 162. The exact relationship is described in more detail below. Stimulation generator 166 receives the output of duty cycle timing circuit 164 and generates an output burst of energy corresponding to each of the output pulses of duty cycle timing circuit 164. The number of pulses in this burst is determined in part by the output of signal processor 152 such that additional pulses are added to the burst when the anticipated cardiac demand becomes high.

Conditioning generator 168 supplies conditioning pulses as needed. The stimulation pulses of stimulation generator 166 are combined with the conditioning pulses of conditioning generator 168 and supplied to skeletal muscle 22 by stimulation lead 32.

An alternative implementation of implantable pulse generator 36 is through the use of a microprocessor controlled general purpose implantable pulse generator such as PROMETHEUS ® pulse generator manufactured by Medtronic, B.V. of the Netherlands. The primary advantage of such as implementation is the ease with which such a programmable device can change modes of operation. This is particularly useful when doing clinical research. A description of the use of such a device may be found in the paper "Pulse Generator for Biomechanical Cardiac Assistance by Counter-Pulsation Technique", by Grandjean, et al., published in the "Record of the Conference on Skeletal Muscle for Cardiac Assist and Repair, Banff Sept. 28–Oct. 2, 1988", published by Futura Editions (August 1989).

Figure 5:
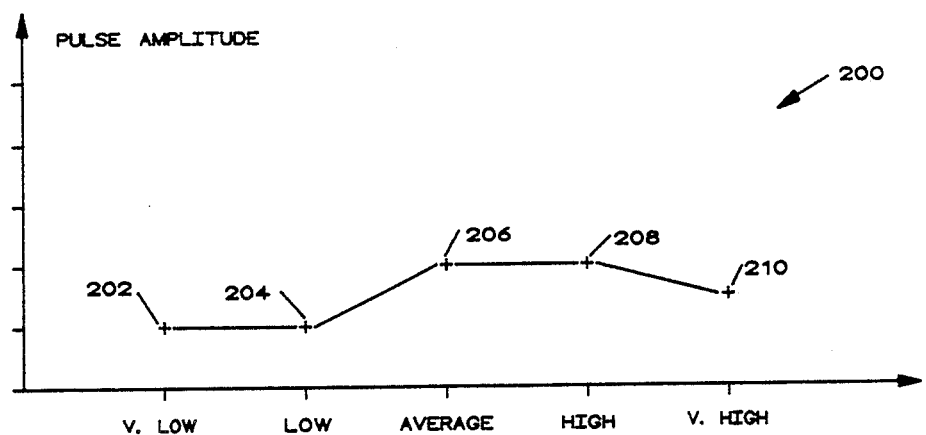
FIG. 5 is a graphical representation of stimulation pulse amplitude as a function of cardiac demand.

FIG. 5 is a graphical representation of a relationship between the pulse amplitude and the anticipated cardiac demand. In this case anticipated cardiac demand corresponds to the appropriate cardiac rate which is determined from the output of activity sensor 104. This is computed in the manner known in the art from U.S. Pat. No. 4,379,402 issued to Anderson, et al. As can be seen, points 202 and 204 correspond to very low and low anticipated cardiac demand, respectively. These are on the order of less than 70 beats per minute. At these rates, stimulation generator 166 supplies output pulses of minimum amplitude. These pulses must be greater than the stimulation threshold of skeletal muscle 22. However, considerable energy is saved through using an amplitude which is only slightly greater than this threshold.

Points 206 and 208 correspond to average and high anticipated cardiac demand, respectively. These correspond to rates in the range of 70 to 120 beats per minute although the exact values are patient dependent. At this demand level, the cardiac loading is sufficient to benefit from the additional amplitude and therefore additional assurance of capture. Point 210 is above 120 pulses per minute for most patients. Again notice that this is the anticipated cardiac demand and not the actual heart rate.

Figure 6:
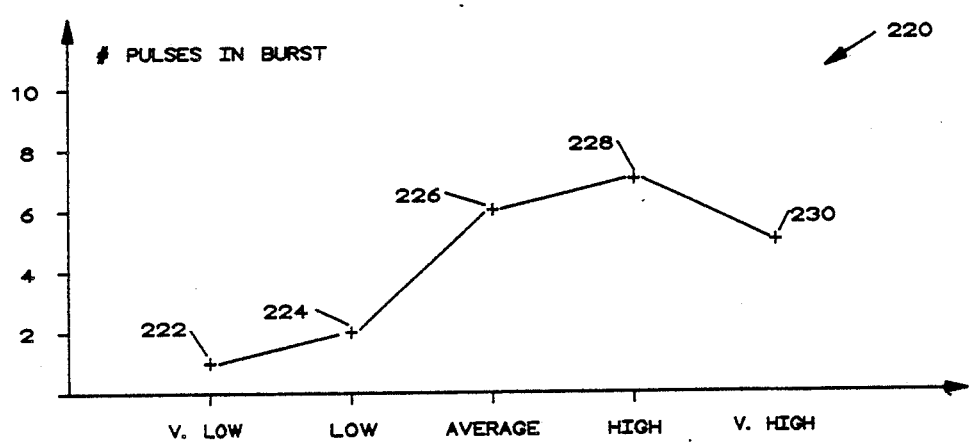
FIG. 6 is a graphical representation of number of stimulation pulses per burst at a function of cardiac demand.

FIG. 6 is a graphical representation of the number of pulses in a given stimulation burst as a function of anticipated cardiac demand. The ranges along the abscissa are as explained above for most patients. Average and high anticipated cardiac demand again require the greatest number of pulses per burst and therefore the highest energy demand. The number of pulses per burst is decreased at very high anticipated demands because efficiency is impaired if the individual pulse occur too frequently.

Figure 7:
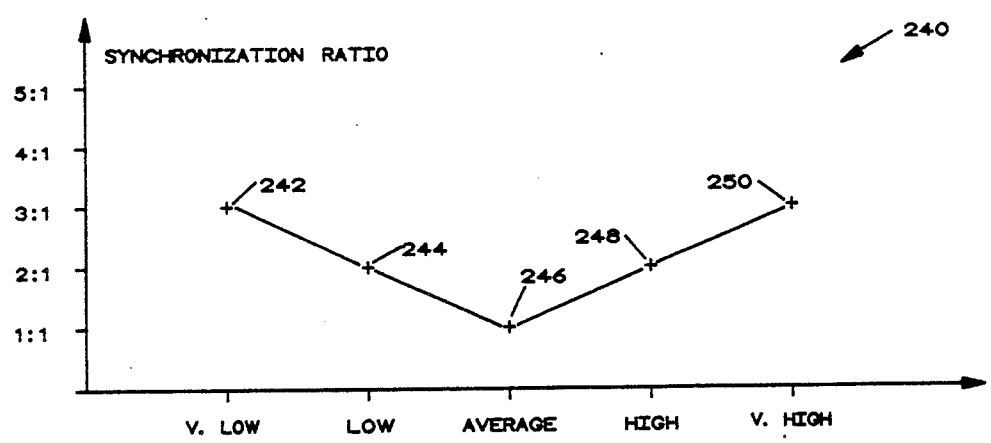
FIG. 7 is a graphical representation of synchronization ratio.

FIG. 7 is a graphical representation of the synchronization ratio performed by the variable counter of duty cycle timing circuit 164. A one-to-one synchronization ratio is used for average anticipated cardiac demand. This provides the greatest chronic assistance to the myocardium with the least battery consumption by implantable pulse generator 36. The synchronization ratio is greater for less than average anticipated cardiac demand because less assistance is actually required. The synchronization ratio increases as the anticipated cardiac demand increases to ensure the fatigue of skeletal muscle 22 is minimized.

Figure 8:
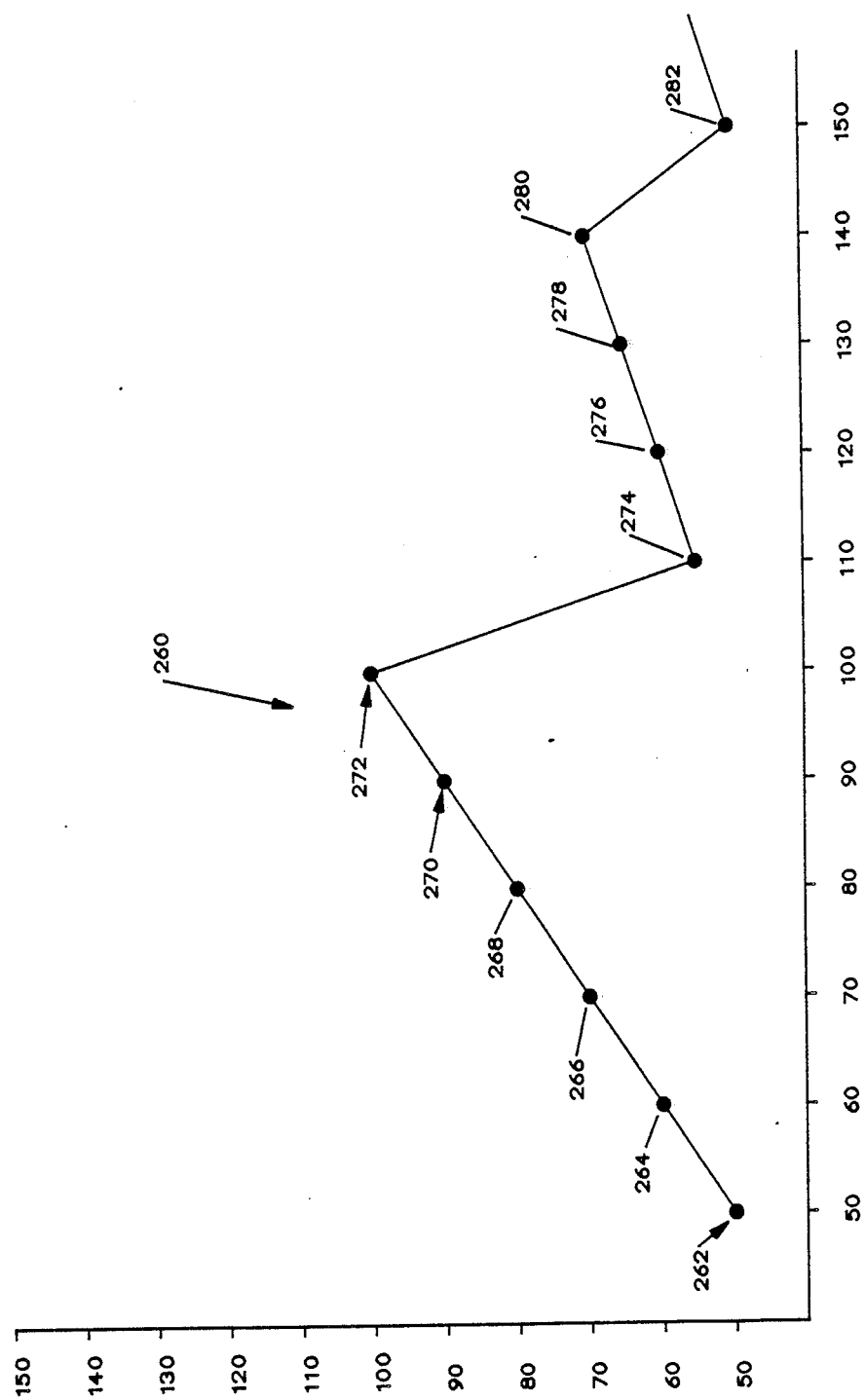
FIG. 8 is a graphical representation of stimulation rate as a function of cardiac rate.

FIG. 8 is a graphical representation of actual cardiac rates on the ordinate in relation to actual rates of stimulation of skeletal muscle 22 along the ordinate abscissa. Shown is the change in duty cycle with actual rate. The duty cycle is one-for-one (e.g., points 262, 264, 266, 268, 270 and 272) in the typical patient in the range of 50 to 100 beats per minute. At point 272, the actual cardiac rate is 100 beats per minute and the rate of stimulation of skeletal muscle 22 is 100 beats per minute. Above that rate, skeletal muscle 22 is stimulated only once for every two cardiac cycles (e.g., see points 274, 276, 278, and 280). At point 280 (140 beats per minute), the duty cycle becomes one stimulation of skeletal muscle 22 for every three cardiac cycles (e.g., see point 282).

Having thus described the preferred embodiments of the present invention, those of skill in the art will be able to readily apply these teachings to other embodiments without deviating from the scope of the claims hereto attached.

I claim:

1. Apparatus comprising:
   a. a surgically prepared skeletal muscle adapted to be mechanically coupled to a natural human heart having ventricles which contract at a ventricular rate such that contraction of said surgically prepared skeletal muscle assists said natural human heart;
   b. means responsively coupled to said natural human heart and said surgically prepared skeletal muscle for stimulating said skeletal muscle in synchrony with contraction of said ventricles of said natural human heart, said stimulation having parameters including pulse amplitude, duty cycle, pulses per burst, pulse width, and pulse interval; and
   c. means responsively coupled to said stimulating means and adapted to be connected to a human body for sensing anticipated cardiac demand.

2. Apparatus according to claim 1 further comprising:
   means responsively coupled to said stimulating means and said sensing means for varying at least one of said parameters of stimulation of said stimulating means.

3. Apparatus according to claim 2 wherein said at least one of said parameters of stimulation includes pulse amplitude.

4. Apparatus according to claim 2 wherein said at least one of said parameters of stimulation includes duty cycle.

5. Apparatus according to claim 2 wherein said at least one of said parameters of stimulation includes number of pulses per burst.

6. Apparatus according to claim 2 wherein said at least one of said parameters of stimulation includes pulse width.

7. Apparatus according to claim 2 wherein said at least one of said parameters of stimulation includes pulse interval.

8. A method of assisting cardiac activity of a natural human heart having ventricles which contract at a ventricular rate comprising:
   a. surgically preparing a skeletal muscle;
   b. positioning said skeletal muscle such that contraction of said skeletal muscle synchronously with contraction of said ventricles assists said cardiac activity;
   c. determining anticipated cardiac demand; and
   d. stimulating said skeletal muscle to contract synchronously with contraction of said centricles in accordance with said anticipated cardiac demand.

9. A method according to claim 8 wherein said determining anticipated cardiac demand includes sensing body activity.

* * * * *

UNITED STATES PATENT AND TRADEMARK OFFICE
CERTIFICATE OF CORRECTION

PATENT NO. : 5,069,680
DATED : December 3, 1991
INVENTOR(S) : Pierre-Andre Grandjean It is certified that error appears in the above-identified patent and that said Letters Patent is hereby corrected as shown below:

On the cover page, second column, at paragraph numbered "56", the OTHER PUBLICATION should be "Heart Transplantation". The word "Heart" is misspelled.
At Column 6, line 63, replace "centricles" with --ventricles--.

Signed and Sealed this

Eighteenth Day of May, 1993

*Attest:*

MICHAEL K. KIRK

*Attesting Officer*   Acting Commissioner of Patents and Trademarks

UNITED STATES PATENT AND TRADEMARK OFFICE
CERTIFICATE OF CORRECTION

PATENT NO. : 5,069,680
DATED : December 3, 1991
INVENTOR(S) : Pierre-Andre Grandjean It is certified that error appears in the above-indentified patent and that said Letters Patent is hereby corrected as shown below:

Column 1, Line 7, delete "07/446,599,", and insert in its place --07/446,594--.

Column 1, Line 8, after "Dec. 6, 1989,", delete --pending--.

Column 1, Line 10, after "Dec. 6, 1989,", delete --pending--.

Column 1, Line 13, after "Dec. 6, 1989,", delete --pending--.

Column 2, Lines 66-67, after "pulse amplitude,", delete --pulse width, pulse interval,--.

Column 4, Line 2, delete "t e", and insert in its place --the--.

Column 4, Line 53, delete "sown", and insert in its place --shown--.

Column 6, Line 66, delete "centricles", and insert in its place --ventricles--.

Signed and Sealed this

Eighteenth Day of October, 1994

Attest:

BRUCE LEHMAN

Attesting Officer

Commissioner of Patents and Trademarks